United States Patent [19]
Cohen

[11] 4,450,957
[45] May 29, 1984

[54] DENTAL CAPSULE

[75] Inventor: Gordon S. Cohen, Orange, Conn.

[73] Assignee: Jeneric Industries, Inc., Wallingford, Conn.

[21] Appl. No.: 458,888

[22] Filed: Jan. 18, 1983

[51] Int. Cl.³ .................. B01F 3/12; B65D 25/08; B65D 81/32
[52] U.S. Cl. .................. 206/220; 206/63.5; 206/222; 215/DIG. 8
[58] Field of Search .................. 206/63.5, 219, 220, 206/221, 222, 568; 215/6, DIG. 8; 366/602

[56] References Cited

U.S. PATENT DOCUMENTS

| | | | |
|---|---|---|---|
| 2,487,236 | 11/1949 | Greenberg | 206/47 |
| 2,527,991 | 10/1950 | Greenberg | 206/47 |
| 2,527,992 | 10/1950 | Greenberg | 206/47 |
| 3,139,180 | 6/1964 | Kobernick | 206/47 |
| 3,185,462 | 5/1965 | Shore | 366/602 |
| 3,275,302 | 9/1966 | Horton | 259/72 |
| 3,290,017 | 12/1966 | Davies et al. | 259/114 |
| 3,357,545 | 12/1967 | Kobernick | 206/47 |
| 3,415,360 | 12/1968 | Baumann et al. | 206/219 |
| 3,425,598 | 2/1969 | Kobernick | 222/83 |
| 3,451,540 | 6/1969 | Kulischenko | 206/47 |
| 3,625,349 | 12/1971 | Muhlbauer | 206/47 A |
| 3,638,918 | 2/1972 | Denholtz | 259/48 |
| 3,651,932 | 3/1972 | Muhlbauer | 206/47 A |
| 3,655,035 | 4/1972 | Muhlbauer | 206/47 A |
| 3,655,037 | 4/1972 | Lussler | 206/635 |
| 3,796,303 | 3/1974 | Allet-Coche | 206/47 |
| 3,815,878 | 6/1974 | Baskas et al. | 259/37 |
| 3,841,467 | 10/1974 | Hansen | 206/219 |
| 3,963,120 | 6/1976 | Perfect | 206/219 |
| 3,986,834 | 10/1976 | Steinbrink, Jr. | 23/230 |
| 4,002,235 | 1/1977 | Donnelly | 206/219 |
| 4,142,629 | 3/1979 | Biondo et al. | 206/219 |
| 4,182,447 | 1/1980 | Kay | 206/219 |
| 4,185,740 | 1/1980 | Perfect | 206/220 |
| 4,306,651 | 12/1981 | Muhlbauer | 206/219 |

FOREIGN PATENT DOCUMENTS

| | | | |
|---|---|---|---|
| 495928 | 1/1976 | Australia | 206/219 |
| 519008 | 4/1953 | Belgium . | |
| 354351 | 6/1961 | Switzerland . | |
| 1180181 | 2/1970 | United Kingdom . | |
| 2027601 | 2/1980 | United Kingdom . | |

*Primary Examiner*—George E. Lowrance
*Assistant Examiner*—Jimmy G. Foster
*Attorney, Agent, or Firm*—Barry Kramer

[57] ABSTRACT

A self-actuating dental capsule is provided which includes a rupturable container for the liquid component of a dental amalgam. The container is held in the capsule by a retaining sleeve or disk so that the amalgam can be immediately used by the dentist without the need to separate the container from the amalgam. The container and the retaining means can be formed as a unit prior to placement in the capsule.

3 Claims, 5 Drawing Figures

DENTAL CAPSULE

BACKGROUND OF THE INVENTION

1. Field of The Invention

This invention relates to dental capsules and in particular to dental capsules of the self-actuating type.

2. Description of the Prior Art

Dental amalgam fillings are produced by mixing together a liquid component, e.g. mercury, and a powdered component, e.g. silver or a silver alloy. Dental capsules are used both to hold the liquid and powdered components separate from each other during shipping and storage and as a mixing chamber for mixing the liquid and powdered components together to form the amalgam.

Over the years, numerous dental capsules have been proposed. These capsules differ from one another both in the means used to hold the liquid component and in the means used to release this component for mixing with the powdered component. In the past, releasing of the liquid has required some manual manipulation of the capsule by the dentist. For example, in some prior art capsules, it was necessary to rotate a portion of the capsule to release the mercury. Other capsules employed telescoping members whereby the movement of one member past another released the mercury. Other mechanisms, including cutting a sack of mercury with a sharp blade, have been suggested.

Recently, dental capsules which are self-actuating have become available. With these types of capsules, a separate step is not required to release the mercury for mixing with the powdered component of the amalgam. Rather, the mercury is automatically released during vibration of the capsule in an amalgamator.

One such capsule is shown in U.S. Pat. No. 4,306,651. In accordance with this patent, the mercury is encapsulated in a foil bag and the bag and powder are placed together in the dental capsule. When the capsule is vibrated in an amalgamator, the foil bag ruptures allowing the mercury to mix with the powder. This design has a number of drawbacks. For example, a portion of the mercury can remain inside the bag after vibration in the amalgamator, thus causing variations in the chemical composition of the amalgam. Moreover, the bag tends to stick to the amalgam and thus must be removed from the amalgam by the dentist before the filling material is inserted in a patient's tooth. Since there is a limited amount of time during which the amalgam can be used after the mercury and the powder have been combined, this extra step of removing the bag from the amalgam is undesirable.

Other prior self-actuated capsules, such as those shown in U.S. Pat. No. 4,182,447, U.K. patent application 2,027,601 and Belgium Patent No. 519,008, have similar problems or are difficult to manufacture.

In view of these problems with the prior art self-actuated dental capsules, it is the object of this invention to provide an improved self-actuated dental capsule which is simple to construct, does not require separating the amalgam from the means used for holding the mercury and insures that all of the mercury is mixed with the silver-containing powder.

SUMMARY OF THE INVENTION

In accordance with the invention, an improved self-actuating capsule for a dental amalgam which includes a powdered component and a liquid component is provided. The capsule comprises a chamber for holding the powdered component and for mixing the powdered and liquid components to form the amalgam. Disposed within the chamber is a separate rupturable container for the liquid component of the amalgam. The capsule and the container for the liquid component are designed so that the container remains in the capsule after the amalgam has been formed.

In certain preferred embodiments of the invention the dental capsule is provided with a cylindrically-shaped sleeve which fits snuggly in the capsule and engages the container for the liquid component of the amalgam so as to hold that container within the chamber after the amalgam has been mixed. The container can be provided with a central portion for holding the liquid component of the amalgam and with a skirt surrounding the central portion which is engaged by one end of the cylindrically-shaped sleeve to hold the container near one end of the capsule. The sleeve and the skirt of the container can be united as a unit prior to the placement of the container in the capsule or the container and the sleeve can be separate components, with the container being placed in the capsule first and the sleeve inserted thereafter to engage the skirt and hold the container in the capsule.

In other preferred embodiments, a disk-shaped member which engages a recess in the capsule is used instead of a sleeve to hold the container in the capsule.

In connection with the various embodiments of the invention, a pestle can be employed for breaking the container for the liquid component of the amalgam when the capsule is vibrated in an amalgamator and for insuring that the container is completely emptied of the liquid component.

DESCRIPTION OF THE PREFERRED EMBODIMENTS

Figure 1:
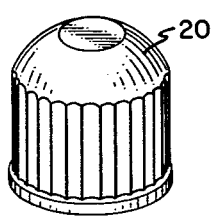
FIG. 1 shows in disassembled form the components of a preferred form of the capsule employing a sleeve to retain the container for the liquid component of the amalgam in the capsule.
Figure 1:
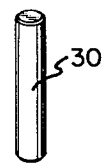
Figure 1:
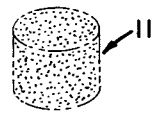
Figure 1:
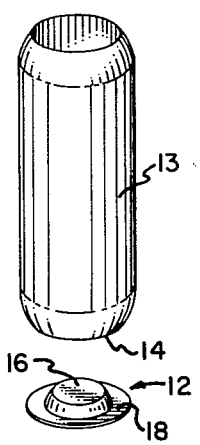
Figure 1:
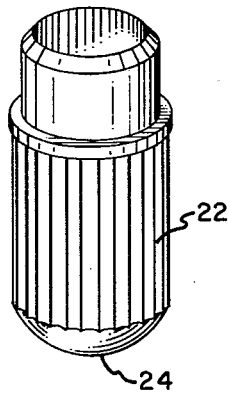

The present invention provides an easy to construct and easy to use self-actuated dental capsule. In particular, the invention eliminates the need to separate the amalgam from the container used to hold the liquid component of the amalgam. Moreover, in accordance with the preferred embodiments of the invention, as described below, construction of the capsule involves only simple to fabricate parts.

As shown in the figures, wherein the same numbers are used to identify similar components of the various embodiments, capsule 8 of the present invention includes cylindrically-shaped chamber 10 for holding powdered component 11 of a dental amalgam during shipping and storage and for mixing the liquid and powdered components together to form a dental amalgam. Within chamber 10 is rupturable container 12 for carrying liquid component 9 of a dental amalgam. In a preferred form of the invention, container 12 consists of central portion 16 for holding liquid component 9 and skirt 18 surrounding the central portion for use in retaining container 12 in chamber 10 as the amalgam is removed. Capsule 8 is formed from two mating cylindrically-shaped portions 20 and 22 which can be separated for removing the amalgam from chamber 10 once the liquid and powdered components have been mixed, as well as for inserting container 12, powder 11 and pestle 30 into chamber 10.

Container 12 for liquid component 9 of the dental amalgam can be retained in chamber 10 by a variety of means. For example, container 12 can be glued, welded or otherwise attached to either one of the two mating cylindrically-shaped portions 20 and 22 making up capsule 8.

Figure 2:
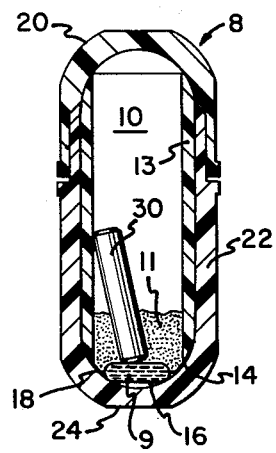
FIG. 2 shows the components of FIG. 1 in their assembled condition.

A preferred method for retaining container 12 within chamber 10 is shown in FIGS. 1 and 2. This embodiment employs elongated cylindrically-shaped sleeve 13 which snuggly fits within the inner walls of capsule 8. Edge 14 of sleeve 13 engages skirt 18 of container 12 to hold container 12 in chamber 10 after the amalgam is formed.

The embodiment shown in FIGS. 1 and 2 has a number of important advantages. First, cylindrically-shaped sleeve 13 is easily constructed. No expensive molding techniques need be employed to prepare this component. Second, sleeve 13 is self-aligning with the walls of capsule 8. Because of its length, sleeve 13 cannot become cocked relative to the inner walls of capsule 8 and is guided by those walls to its final resting position. Third, by being at the outermost periphery of the capsule, sleeve 13 is unlikely to engage container 12 at its liquid containing central portion 16 and thus is unlikely to rupture the container during assembly of the capsule.

The capsule shown in FIGS. 1 and 2 is assembled in the following way. First, using known equipment, container 12 for liquid component 9 is prepared having a skirt 18 of approximately the same diameter as the inside walls of portions 20 and 22 of capsule 8. Container 12 can be made out of a variety of materials including polyethylene, polypropylene, polyamid or similar polymeric materials. Container 12 is preferably formed from two circular disks which are welded together at the edges to enclose liquid 9.

The first step in assembling capsule 8 comprises inserting container 12 into portion 22. Thereafter, sleeve 13 is slid into portion 22 with edge 14 engaging skirt 18 of container 12 and pushing the container towards ends 24 of portion 22. Sleeve 13 is sized so that when portions 20 and 22 of capsule 8 are mated together, sufficient pressure is applied to skirt 18 to hold container 12 in capsule 8 after the amalgam has been prepared.

After container 12 and sleeve 13 are in position, powdered component 11 of the amalgam and pestle 30 are introduced into portion 22. Thereafter, portion 20 is mated with portion 22 to form the completed dental capsule.

Pestle 30 serves both to break container 12 to release liquid component 9 and to aid in mixing of the powdered and liquid components of the amalgam. The presence of pestle 30 inside chamber 10 during the mixing process helps insure that all of liquid component 9 is expelled from container 12 and mixed with powdered component 11 of the amalgam. This helps insure that the amalgam formed is of the correct chemical composition.

Once capsule 8 has been closed, it can be shipped and stored until needed by the dentist. Container 12 for liquid component 9 of the amalgam prevents liquid component 9 from mixing with the powdered component until such time as capsule 8 is to be used. To use capsule 8, the dentist simply inserts the capsule into an amalgamator. The amalgamator vigorously vibrates the capsule causing pestle 30 to stike and rupture container 12. Rupturing of container 12 allows the liquid component 9 of the amalgam to pass out of container 12 and then be mixed by pestle 30 with powdered component 11 of the amalgam.

After the powdered and liquid components of the amalgam have been thoroughly mixed, capsule 8 is opened by separating portions 20 and 22. The amalgam is then removed from capsule 8 and applied to the patient's tooth. Cylindrically-shaped sleeve 13 insures that container 12 does not pass out of capsule 8 with the mixed amalgam.

Figure 3:
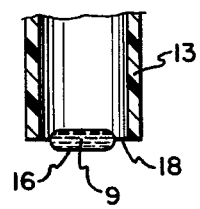
FIG. 3 shows an alternate embodiment of the capsule of FIGS. 1 and 2 wherein the sleeve and the container for the liquid component of the amalgam are united as a unit prior to being placed in the capsule.

An alternative preferred embodiment is shown in FIG. 3. In this embodiment, sleeve 13 and container 12 are combined as a unit prior to insertion thereof into portion 22 of capsule 8. The unit is formed by attaching skirt 18 of container 12 to the bottom of sleeve 13. The attachment can be made in a variety of ways, including gluing or heat sealing skirt 18 to sleeve 13. Heat sealing is considered the preferred method.

Figure 4:
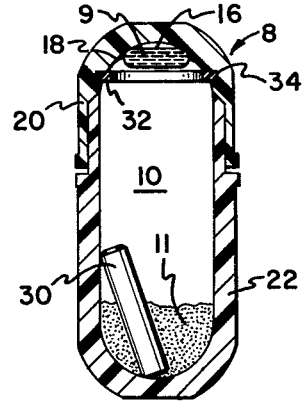
FIG. 4 shows another preferred embodiment of the capsule in which a disk-shaped member having an aperture therein is used to hold the container for the liquid component of the amalgam in the capsule.
Figure 4A:
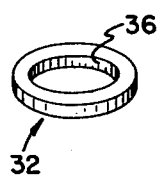
FIG. 4A is a detailed view of the disk-shaped member of FIG. 4.

FIG. 4 shows a further preferred embodiment of the invention. In this embodiment, container 12 is held in capsule 8 by means of disk-shaped member 32 shown in detail in FIG. 4A. Disk-shaped member 32 is held in place in capsule 8 by means of recess or undercut 34 in portion 20 of capsule 8. In turn, disk-shaped member 32 holds container 12 in place by engaging skirt 18 of container 12. Disk-shaped member 32 includes aperture 36 through which pestle 30 passes to rupture container 12 to permit liquid component 9 of the amalgam contained therein to come in contact with and be mixed with powdered component 11.

The capsule of FIG. 4 is assembled as follows. First, container 12 is inserted in portion 20 of capsule 8, following which disk-shaped member 32 is placed into undercut 34. Portion 20 of capsule 8 is preferably made of a resilient material which will give slightly as member 32 is pushed into place and then snap back to securely hold member 32 in place. After container 12 and member 32 are in place, pestle 30 and powdered component 11 are placed in portion 22 of capsule 8, after which the two portions 20 and 22 are combined to form the completed capsule.

Although specific embodiments of the invention have been illustrated, it is to be understood that modifications to the invention can be made without departing from its spirit or scope. In particular, other means besides those illustrated can be used to retain the container for the liquid component of the amalgam within the capsule after the amalgam has been mixed. Similarly, the various components of the capsule can have a variety of configurations and sizes and the components of the capsule can be assembled in orders other than the orders illustrated herein.

What is claimed is:

1. A capsule holding a dental amalgam including a powdered component and a liquid component, said capsule comprising:
   a chamber having a wall housing the powdered component and for mixing the powdered and liquid components together to form the amalgam;
   a rupturable container holding the liquid component of the amalgam disposed within said chamber;
   said rupturable container including a central portion which holds the liquid component and a skirt surrounding said central portion;
   means for opening the chamber to remove the amalgam after the powdered and liquid components have been mixed together;
   a pestle for rupturing the container and mixing together the powdered and liquid components of the amalgam when the capsule is vibrated in a dental amalgamator; and
   means disposed within the chamber for holding said skirt portion of said container within said chamber and retaining the container for the liquid component within the chamber as the amalgam is removed from the chamber, said holding means including
   a cylindrically-shaped sleeve having a centrally located opening larger in diameter than the central portion of said rupturable container and a wall portion provided with a lower edge in contact with the skirt portion of said container to hold the same against the wall of said chamber,
   whereby upon assembly of said capsule, the sleeve will not engage the central portion of said container to rupture the same, while holding the container so it can be ruptured by passage of said pestle therethrough into contact with the central portion of said container.

2. The apparatus of claim 1 wherein the skirt portion of said container and the lower edge of said sleeve are formed as a unit, apart from said chamber, and the unit is disposed in the capsule.

3. A capsule holding a dental amalgam including a powdered component and a liquid component, said capsule comprising:
   a chamber having a wall housing the powdered component and for mixing the powdered and liquid components together to form the amalgam;
   a rupturable container holding the liquid component of the amalgam disposed within said chamber;
   said rupturable container including a central portion which holds the liquid component and a skirt surrounding said central portion;
   means for opening the chamber to remove the amalgam after the powdered and liquid components have been mixed together;
   a pestle for rupturing the container and mixing together the powdered and liquid components of the amalgam when the capsule is vibrated in a dental amalgamator,
   means disposed within the chamber for holding said skirt portion of said container within said chamber and retaining the container for the liquid component within the chamber as the amalgam is removed from the chamber, said holding means including
   a disc-shaped member held in a recess formed in the wall of said chamber, said disc-shaped member engaging the skirt portion of said container to retain the skirt portion of said container in said recess and said container in said chamber, said disc-shaped member having a centrally located opening larger in diameter than the central portion of said rupturable container,
   whereby upon assembly of said capsule, the disc-shaped member will not engage the central portion of said container to rupture the same, while holding the container so that it can be ruptured by passage of said pestle therethrough into contact with the central portion of said container.

* * * * *